(12) United States Patent
Zappala

(10) Patent No.: US 6,423,072 B1
(45) Date of Patent: Jul. 23, 2002

(54) BONE ANCHOR DELIVERY DEVICE WITH AN ARTICULATING HEAD

(76) Inventor: Stephen M. Zappala, 98 Rattlesnake Hill Rd., Andover, MA (US) 01810

(*) Notice: Subject to any disclaimer, the term of this patent is extended or adjusted under 35 U.S.C. 154(b) by 0 days.

(21) Appl. No.: 09/574,927

(22) Filed: May 19, 2000

Related U.S. Application Data

(60) Provisional application No. 60/134,857, filed on May 19, 1999.

(51) Int. Cl.[7] .................................................. A61B 17/88
(52) U.S. Cl. ........................................ 606/104; 606/72
(58) Field of Search ........................ 606/72, 73, 104, 606/139, 213, 232

(56) References Cited

U.S. PATENT DOCUMENTS 5,972,000 A * 10/1999 Beyer et al. ................ 606/139
5,988,171 A * 11/1999 Sohn et al. .................. 128/848
6,241,736 B1 * 6/2001 Sater et al. .................. 606/104

OTHER PUBLICATIONS

Influence Medical Technologies Ltd., "in–Fast" Product Brochure, 1998.

\* cited by examiner

*Primary Examiner*—David O. Reip
(74) *Attorney, Agent, or Firm*—Mirick, O'Connell, DeMallie & Lougee, LLP

(57) ABSTRACT

A delivery device for fixing an anchor to a bone which features: a distal delivery member which includes, an articulating head, a bone anchor attached to a suture, and a joint for articulating the head relative to the hand piece; and a proximal hand piece which includes a power source, a motor and a torquing member for driving the anchor into the bone, and one or more corresponding members for attaching the distal delivery member to the hand piece.

20 Claims, 5 Drawing Sheets

BONE ANCHOR DELIVERY DEVICE WITH AN ARTICULATING HEAD

This application claims priority from Provisional application Ser. No. 60/134,857, filed May 19, 1999.

FIELD OF THE INVENTION

This invention relates to bone anchor delivery devices and more specifically to a bone anchor delivery device having an articulating head.

BACKGROUND OF THE INVENTION

Bone anchors are used in connection with various surgical procedures to internally anchor one or more sutures to a bone substrate. For example, bone anchors are used in cystourethropexy and vaginal sling procedures to anchor sutures used in connection with a variety of sling materials to manage urinary incontinence. Traditionally, bone anchors, or bone screws as they are alternatively called, are fixed to the bone by making an incision through the soft tissue, such as the vaginal mucosa, driving the anchor into the pubic bone using a drill and suturing the incision closed. However, this procedure is time consuming and difficult to accomplish through the vaginal opening. Not only must the surgeon close the mucosal incision, the procedure presents a technically difficult suturing angle. As a result, the tension application of the graft on the urethra is usually less than optimal.

To reduce the difficulties associated with the traditional suturing angle, various bone anchor delivery devices were developed, such as the "In-Fast" device available from American Medical Systems, Minnetonka, Minnesota, which features a rigid, offset U-shape design with an additional handle and a screw positioned at the shorter tip of the "U". The U-shape creates a 90 degree angle to allow the lower portion of the device to be inserted into the vagina and pressed against the posterior pubic bone. An actuator located on the hand is then triggered and the bone screw is screwed into the pubic bone directly through the soft, mucosal tissue.

Although currently available bone anchor delivery devices, such as the "In-Fast" device improve somewhat on the traditional procedure, these rigid devices do not provide the necessary flexibility needed to adequately accommodate anatomical variations among patients. For example, these rigid devices do not allow the surgeon to adjust the angle of the screw relative to the handle as needed to negotiate the variety of anatomical variations within female pelves. These rigid devices also restrict the placement of bone-anchors in those women with a large pre-pubic amount of adipose tissue and those with a narrow pubic arch.

SUMMARY OF THE INVENTION

It is therefore a primary object of this invention to provide a bone anchor delivery device with an articulating head.

It is a further object of this invention to provide a bone anchor delivery device which enables the surgeon to vary the angle between the handle and the bone anchor to accommodate various surgical procedures and to negotiate the variety of anatomical variations within female pelves.

It is a further object of this invention to provide a bone anchor delivery device which enables the surgeon to adjust the placement of bone-anchors in those women with a large pre-pubic amount of adipose tissue nor those with a narrow pubic arch.

It is a further object of this invention to provide a delivery device for a bone anchor attached to a suture which includes a self-securing cinch and/or crimp to obviate the need to tie off the suture.

It is a further object of this invention to provide a self-contained, bone anchor delivery device with an articulating head that includes a power source, a motor and a drive shaft for the bone anchor.

It is further object of this invention to provide a bone anchor delivery device with a disposable, articulating head.

It is further object of this invention to provide a bone anchor delivery device that improves the tension on the resulting graft.

The preferred embodiment of the delivery device of the invention for fixing an anchor to a bone, comprises: a distal delivery member which comprises, an articulating head, a bone anchor attached to a suture, and a means for articulating the head relative to the hand piece; and a proximal hand piece which comprises a means for driving the anchor into the bone and a means for attaching the distal delivery member to the hand piece; wherein the means for driving preferably comprises a motor, and a torquing device and the hand piece preferably further comprises a self-contained power source, such as a battery.

The head is preferably capable of articulating over at least a range of about 30 degrees in one or more directions and preferably over a range of at least about 30 degrees in at least both a vertical and a horizontal direction in increments of about five degrees. The means for articulating may comprise a ball and socket joint and/or a position locking means such as one or more corresponding splines or detents.

The distal delivery member is preferably disposable and preferably comprises an exit for the suture and the suture preferably comprises a means for securing the suture such as a cinching and/or crimping device.

Another preferred embodiment of the delivery device of the invention for fixing an anchor to a bone, comprises: a distal delivery member which comprises, an articulating head, a bone anchor attached to a suture, a shaft for driving the anchor into the bone, and a means for articulating the head relative to the hand piece in one or more directions; and a proximal hand piece which comprises, a means for attaching the distal delivery member to the hand piece, a motor, and a device for torquing the shaft; wherein the hand piece may further comprises a self-contained power source; and wherein the distal delivery member is preferably disposable.

BRIEF DESCRIPTION OF THE DRAWINGS

Other objects, features and advantages will occur to those skilled in the art from the following description of the preferred embodiments and the accompanying drawings in which.

DETAILED DESCRIPTION OF THE PREFERRED EMBODIMENTS

The invention features a self-contained, battery-powered drill with an unique articulating head which implants a permanent anchor into the cortex of bone. The anchor fixates a non-absorbable suspension suture of suitable tensile strength to the bone.

The unique articulating head of the device enables the surgeon to vary the angle between the handle and the bone anchor, thus accommodating various surgical procedures. For example, the adjustability will enable pelvic surgeons and urogynecologists to negotiate the variety of anatomical variations within female pelves. Moreover, the versatility of the fish-hook shape will not restrict the placement of bone-anchors in those women with a large pre-pubic amount of adipose tissue nor those with a narrow pubic arch. The device is under the constant surgical supervision and guidance with proper placement guided by the surgeon's identification of routine anatomical landmarks. One of the varied uses of such bone anchor suture fixators is to complement a variety of sling materials in the management of urinary incontinence.

Figure 1:
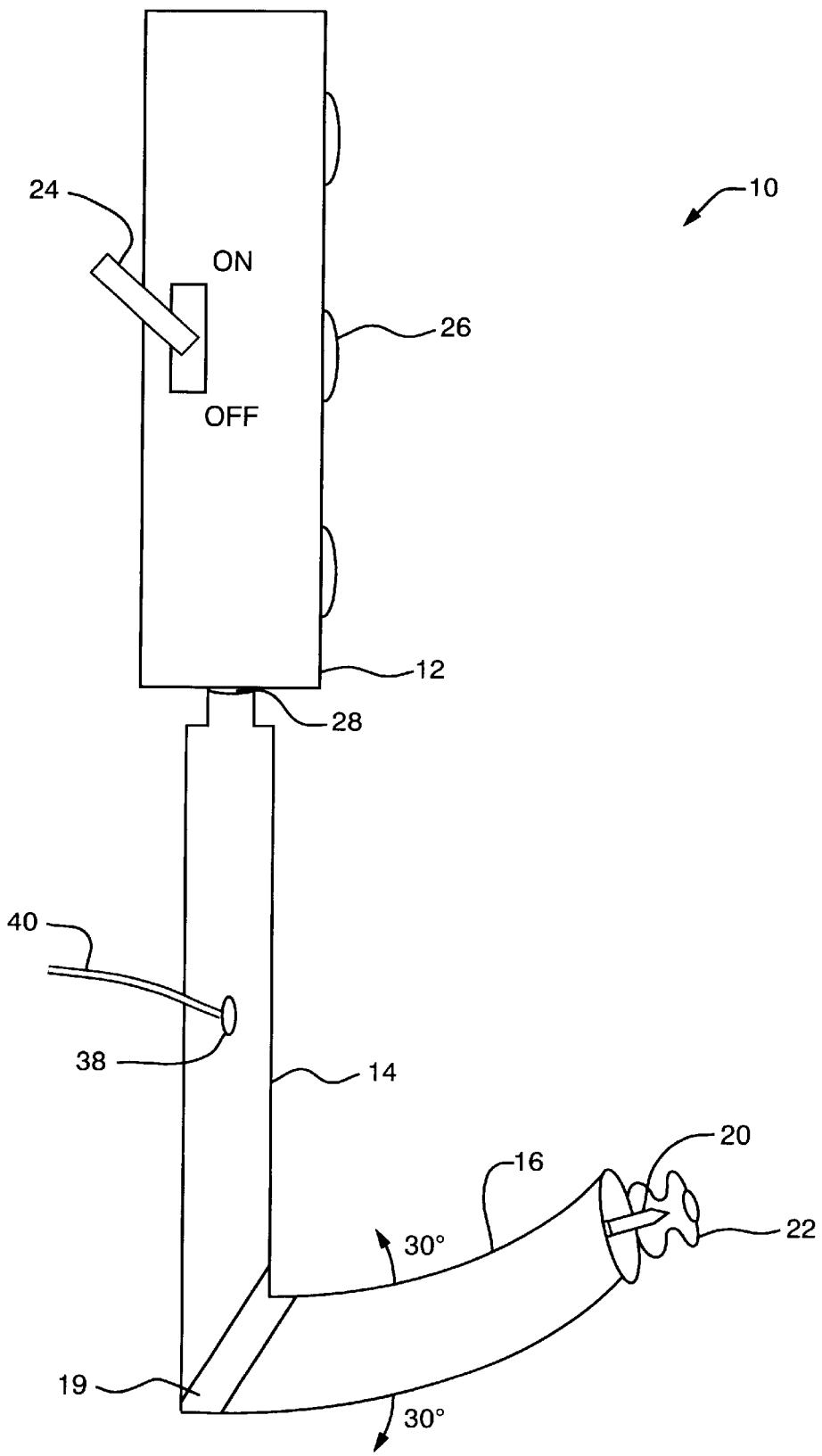
FIG. 1 is a side view of the preferred embodiment of the device of this invention.
Figure 2:
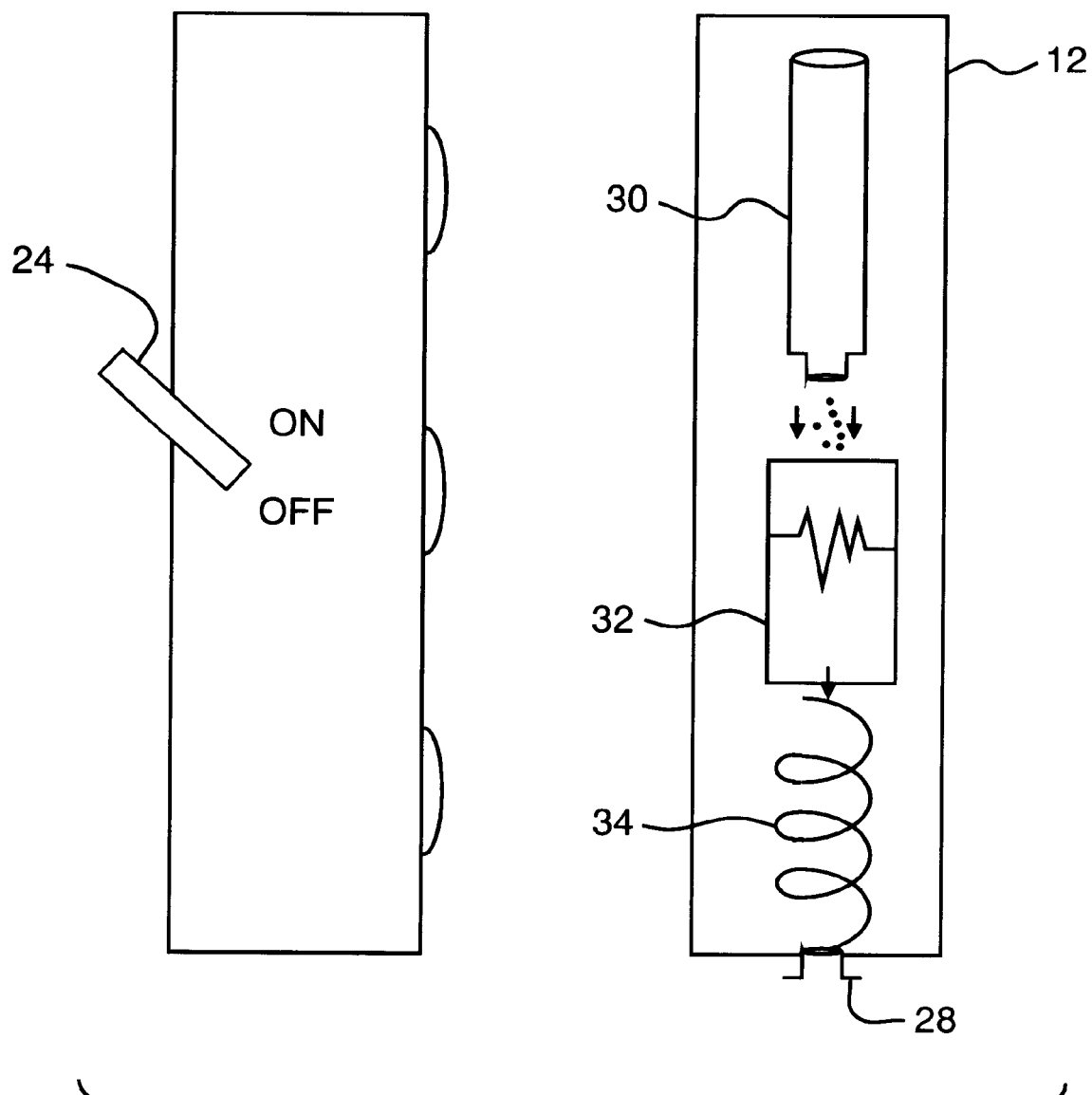
FIG. 2 is a schematic view of the power source, motor and torquing device as housed in the hand piece of the device of the invention.
Figure 4:
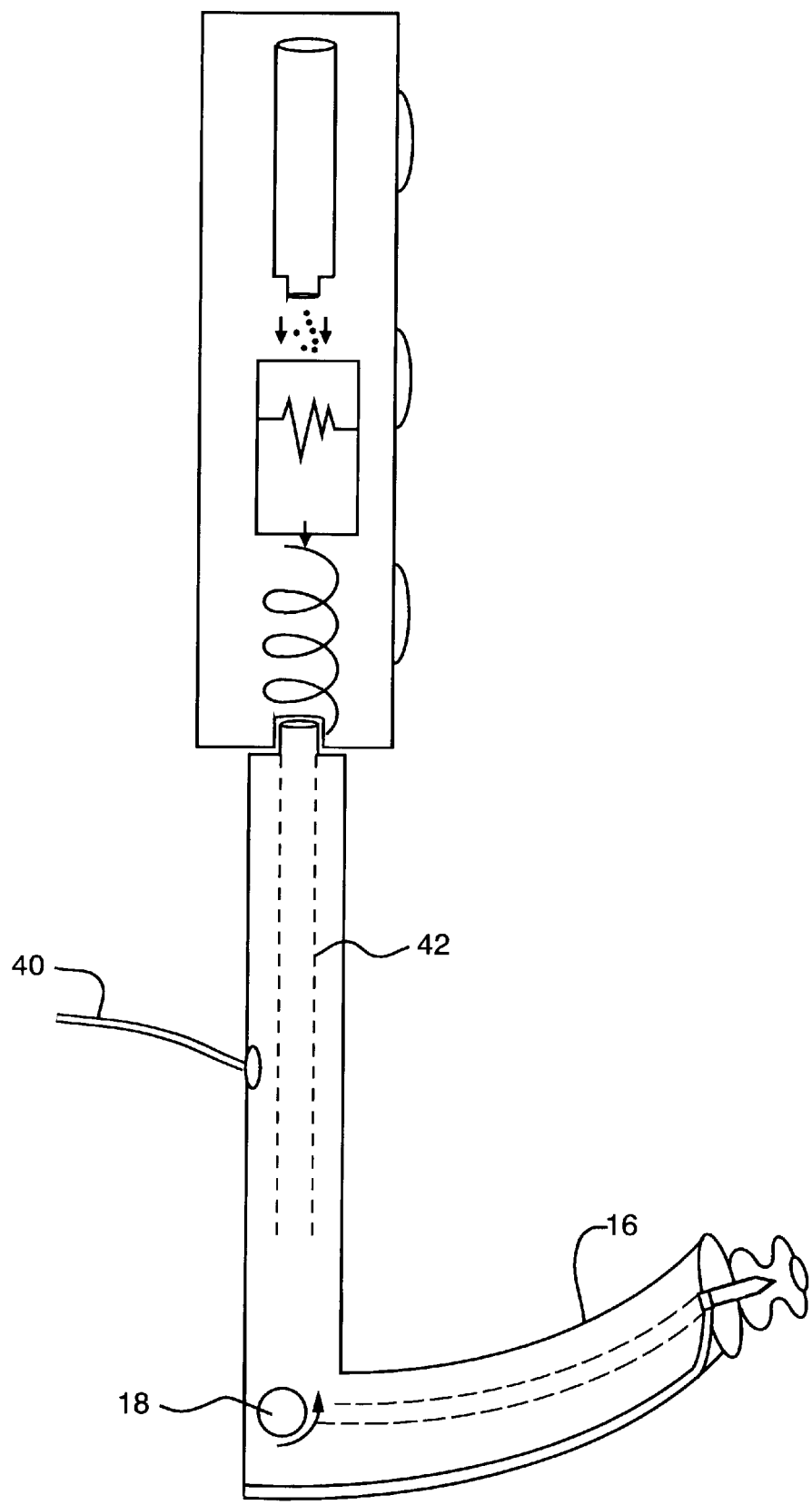
FIG. 4 is a schematic view of the drive shaft, bone anchor attached to a suture and the means for articulating as housed in the distal delivery member of the device of the invention.
Figure 5:
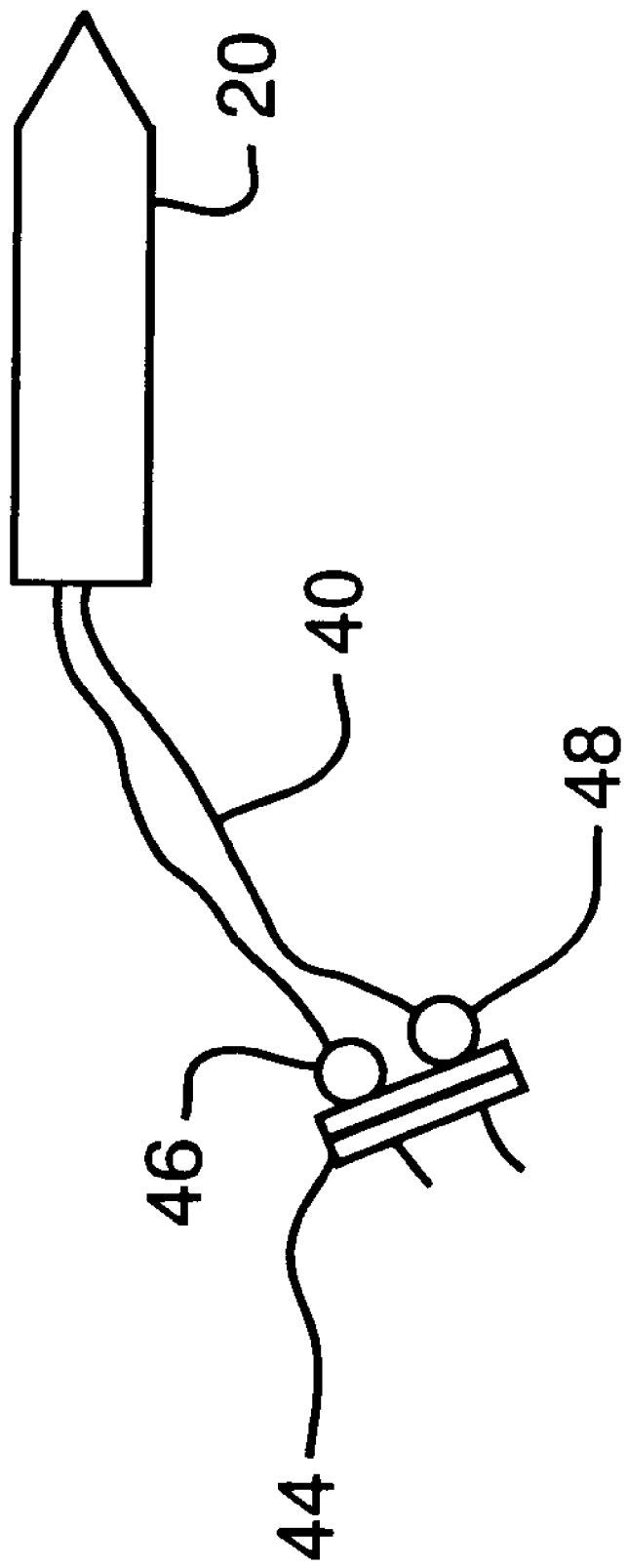
FIG. 5 is a side view of the bone anchor and the means for securing the suture of the device of the invention.

The preferred embodiment of the device is shown in FIG. 1 and generally referred to as device 10. Device 10 is generally fish-hook shaped and articulates at articulating means 18. Light weight device 10 generally comprises two primary sections: proximal hand piece 12, which comprises power source 30 (FIG. 2) and motor 32 (FIG. 2) and torquing means 34 (FIG. 2); and distal delivery member 14, which comprises flexible drive shaft 42 (FIG. 4), articulating head 16, bone anchor 20 attached to suture 40 and a suture securing means 44. In the preferred embodiment, proximal hand piece 12 is a durable, reusable item, and distal delivery member 14 is disposable. As such, distal delivery member is attached and detached from hand piece 12 using means 28 for attaching the distal delivery member to the hand piece. Means 28 may comprise any one or more known means for temporarily connecting to tubular members together including, but not limited to, a releasable tongue and groove connection, compressible spring-loaded mechanism, and/or corresponding threads, Device 10 is preferably adapted to drill a preferably 7 mm diameter, 1 cm long, stainless steel bone anchor 20 into the deep cortex of bone in order to provide a permanent support for non-absorbable sutures. The articulating, snorkel or fish hook contoured system complements the continence procedure described commonly as a pubovaginal sling. Moreover, the complete device includes the suture securing means 44 which preferably is a cinching, synthetic crimp and obviates the conventional tying of the sutures. The locking/cinching device passes up both ends of the anchored sutures and can be applied at the desired location by direct compression of lateral wings 46 and 48.

Device 10 preferably is about twenty-five centimeters (cm) in total length, including a 10 cm long hand piece, 10 cm long portion of distal delivery member that is proximal to articulating means 18, and 5 cm long articulating head. The preferred diameter of hand piece 12 is about 2.5 cm and the preferred maximum transverse diameter distal delivery 20 member 14 is about 1 cm. The device is non-permeable and is constructed of a synthetic, plastic polymer and incorporates a battery, a low-voltage, low-torque motor and a torquing device in hand piece 12 (FIG. 2) which drives flexible shaft 42 which runs through distal delivery member 14, including articulating head 16, and drives bone anchor 20, located at the distal end of shaft 42.

The detachable hand piece 12 is preferably reusable and complements the disposable distal delivery member which comprises flexible shaft 42, compressible mushroom umbrella 22, bone anchor 20, and the articulating head.

Suture 40 is attached to bone anchor 20 as two approximately 15 cm long limbs of non-absorbable suture material. The reusable hand piece is contoured, using raised portions 26, to a surgeon's hand grip and supports lock/unlock switch 24. Switch 24 is engaged after the device is positioned appropriately at the surgical site. Once the switch is engaged (from the "lock" to "unlock" position), the power source is activated, which initiates motor 32 and torquing device 34 which turns shaft 42 to drill bone anchor 20 into the desired location. Metal bone anchor 20 is concealed within an inverted mushroom style, plastic umbrella 22. The protective umbrella collapses, when the distal end of device 10 is pressed against the solid surface of the bony location, to expose the sharp tip of the bone anchor.

Figure 3:
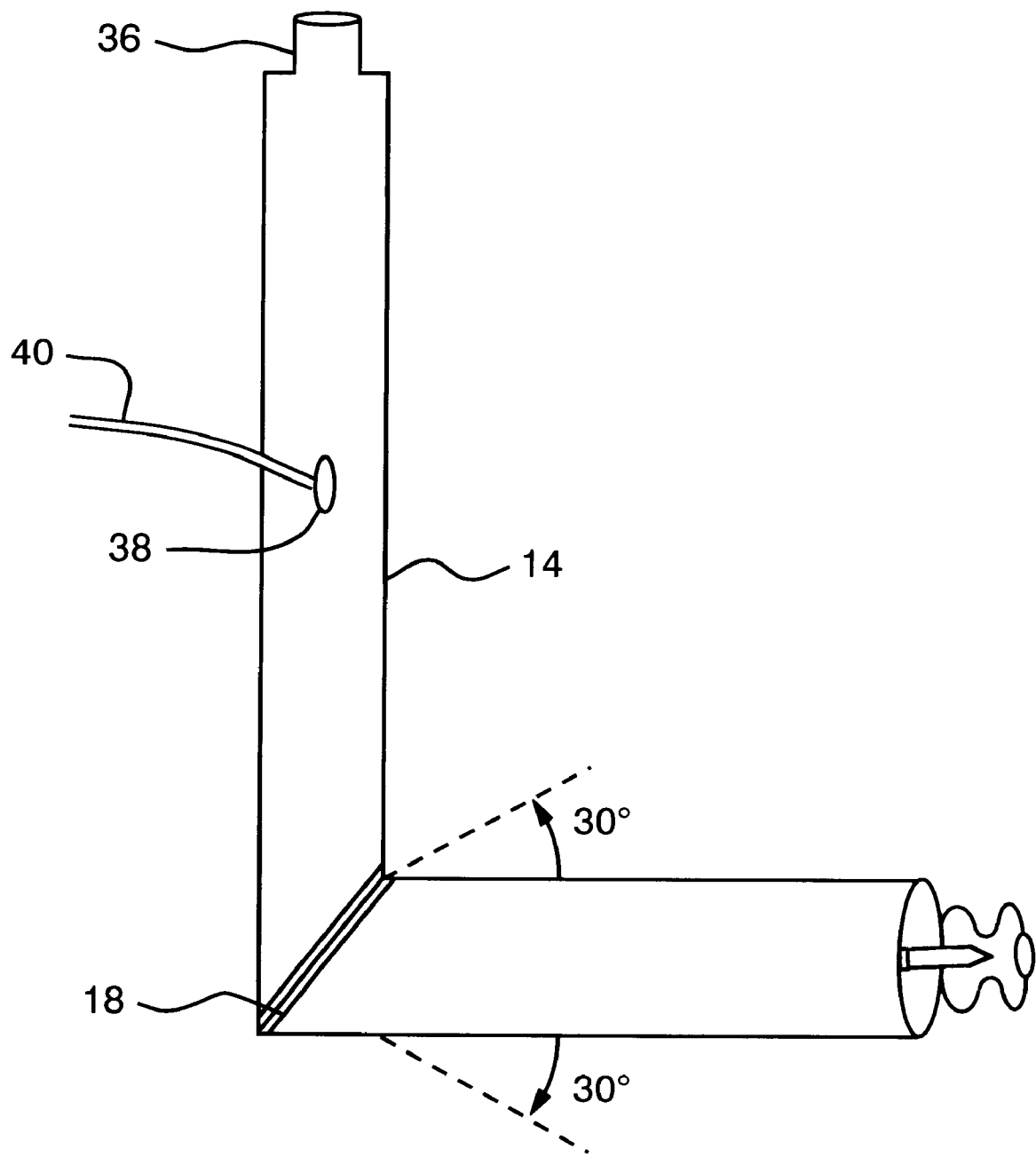
FIG. 3 is a side view of the distal delivery member of the device of the invention.

Distal delivery member 42 includes, at its distal end, a portion of means 18 for articulating head 16 relative to the proximal portion of distal delivery member 14 and hand piece 12. Distal delivery member 42 also preferably includes a position locking means 19. Distal delivery member 42 is preferably constructed of a stainless steel outer casing which houses flexible shaft 42 or other means of providing the motor output torque to bone anchor 20 located at the distal end of articulating head 16. As shown in FIGS. 1 and 3, articulating head 16 preferably articulates over a range of approximately thirty degrees to the left and the right (off center), and thirty degrees in a superior and inferior angle to provide the surgeon with sufficient positioning versatility. However, the degree of articulation could be more or less as required to facilitate a particular surgical procedure. Articulation is preferably accomplished using a ball and socket joint, although, other suitable articulation means may be used.

Position locking means 19 ensures that the desired angle of articulating head 16 is maintained throughout the procedure. Position locking means preferably locks head 16 in positions at five degree increments in all directions of articulation. The position locking means could be achieved in a known mechanical fashion, for example with matching splines, or with appropriately placed detents.

In the urinary incontinence sling procedure, the bone anchor is preferably delivered into the posterior cortex of the symphysis pubis, approximately one centimeter lateral to the urethra which has been identified by the placement of a urethral catheter. The anchor is delivered at the level of the bladder neck, directly into the pubic bone. At a pre-determined amount of torque (power or duration of drilling), a controller in the device ceases delivering power to the anchor. The in situ suture securing means, e.g. cinching plastic crimper 44, obviates a technically difficult suturing angle and conventional ligation of the suture material, and thus enhances the tension application of the graft onto the urethra. The crimper can slide along the sutures so that it holds the graft against the bone. The crimper is operable in a known fashion (for example with a crimping action, or a simple locking/unlocking feature such as in drawstring adjustment devices) to then be tightly held in place. Exit opening 38 is provided in distal delivery member 40 to allow device 10 to be removed after the anchor bone, with suture material attached, is fixed in place.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A delivery device for fixing an anchor to a bone, comprising,
   a distal delivery member which comprises,
      an articulating head, and
      a bone anchor attached to a suture,
   a proximal hand piece which comprises a means for driving said anchor into said bone and a means for attaching said distal delivery member to said hand piece; and
   a means for articulating said head relative to said hand piece.

2. The device of claim 1, wherein said means for driving comprises,
   a motor, and
   a torquing device.

3. The device of claim 2, wherein said hand piece further comprises a self-contained power source.

4. The device of claim 3, wherein said power source comprises a battery.

5. The device of claim 1, wherein said hand piece further comprises a self-contained power source.

6. The device of claim 5, wherein said power source comprises a battery.

7. The device of claim 1, wherein said head is capable of articulating over at least a range of about 30 degrees in one or more directions.

8. The device of claim 7, wherein said head is capable of articulating over a range of at least about 30 degrees in at least both a vertical and a horizontal direction.

9. The device of claim 7, wherein said head is capable of articulating over said 30 degree range in about five degree increments.

10. The device of claim 1, wherein said distal delivery member further comprises an exit for said suture.

11. The device of claim 1, wherein said suture comprises a means for securing said suture.

12. The device of claim 11, wherein said means for securing comprises a cinch.

13. The device of claim 1, wherein said distal delivery member is disposable.

14. The device of claim 1, said means for articulating comprises a ball and socket joint.

15. The device of claim 1, wherein said means for articulating comprising a position locking means.

16. The device of claim 15, wherein said position locking means comprises one or more corresponding splines.

17. The device of claim 16, wherein said position locking means comprises one or more detents.

18. A delivery device for fixing an anchor to a bone, comprising,
   a distal delivery member which comprises,
      an articulating head,
      a bone anchor attached to a suture,
      a shaft for driving said anchor into said bone, and
      a means for articulating said head relative to said hand piece in one or more directions; and
   a proximal hand piece which comprises,
      a means for attaching said distal delivery member to said hand piece,
      a motor, and
      a device for torquing said shaft.

19. The device of claim 18, wherein said hand piece further comprises a self-contained power source.

20. The device of claim 18, wherein said distal delivery member is disposable.

* * * * *